United States Patent
Fox

(10) Patent No.: US 6,657,003 B2
(45) Date of Patent: Dec. 2, 2003

(54) CELL ADHESION SOLUTION

(75) Inventor: William Alan Fox, Burlington, NC (US)

(73) Assignee: Tripath Imaging, Inc., Burlington, NC (US)

( * ) Notice: Subject to any disclaimer, the term of this patent is extended or adjusted under 35 U.S.C. 154(b) by 0 days.

(21) Appl. No.: 09/923,853

(22) Filed: Aug. 7, 2001

(65) Prior Publication Data

US 2002/0051849 A1 May 2, 2002

Related U.S. Application Data

(60) Provisional application No. 60/224,469, filed on Aug. 10, 2000.

(51) Int. Cl.$^7$ .............................. C08L 89/00; C08J 3/24; C08J 8/00
(52) U.S. Cl. ........................ 524/797; 523/105; 524/608; 435/180; 528/493
(58) Field of Search .......................... 523/105; 524/608, 524/797; 435/180; 528/493

(56) References Cited

U.S. PATENT DOCUMENTS

| | | | |
|---|---|---|---|
| 4,894,339 A | * | 1/1990 | Hanazato et al. |
| 5,244,787 A | * | 9/1993 | Key et al. |
| 5,505,952 A | | 4/1996 | Jiang |

FOREIGN PATENT DOCUMENTS

| | | |
|---|---|---|
| EP | 0856539 | 5/1998 |
| JP | 08296177 A | 12/1996 |

OTHER PUBLICATIONS

West, Latour and Hench, "Molecular modeling study of adsorption of poly–L–lysine onto silica glass," CCC 0021–0304/97/040585–07, 1997, John Wiley & Sons Inc.

Chen X et al: "Universal isolation of cross–linked peptides: application to neurofibrillary tangles." Bioconjugate Chemistry. United States Jan.–Feb. 1999, vol. 10, No. 1, pp. 112–118, XPOO2216566 ISSN: 1043–1802.

Mege J L et al: "Use of cell contour analysis to evaluate the affinity between macrophages and glutaraldehyde–treated erythrocytes." Biophysical Journal. United States Aug. 1987, vol. 52, No. 2, pp. 117–186, XPOO2216567 ISSN: 006–3495.

Volkov V S et al: "Interaction of Monomeric Components of Nucleic–Acids with Histone and Poly Lysine in Presence of Formaldehyde" Biochemistry (English Translation of Biokhimiya), vol. 46. No. 10 Part 2, 1981, pp. 1448–1453, XPOO1106229 ISSN: 0006–2979.

Winblade N D et al: "Blocking adhesion to cell and tissue surfaces by the chemisorption of a poly–L–lysine–graft–(poly(ethylene glycol); phenylboronic acid) copolymer." Biomacromolecules. United States 2000 Winter,.

Mcconachie A et al: "The effect on bioadhesive polymers either freely in solution or covalently attached to a support on human macrophages." Biomedical Sciences Instrumentation. United States 1999, vol. 35, 1999, pp. 45–50, XPOO2216569 ISSN: 0067–8856.

Melius P: "Structure of Thermal Polymers of Amino–Acids" Biosystems, vol. 15, No. 4, 1982, pp. 275–280, XPOO2216570 ISSN: 0303–2647.

Watts et al., "The Use of Cationic Polyelectrolytes in the Preparation of Cell Monolayers for AutomatedCell Scanning and Diagnostic Cytopathology," 272–278, Analytical and Quantitative Cytology (1984).

Chapter IV, The Chemistry of Fixation, Reference book, poblisher and date unknown.

\* cited by examiner

Primary Examiner—Tae H. Yoon
(74) Attorney, Agent, or Firm—George A. Leone

(57) ABSTRACT

A cell adhesion solution of a cross-linked polymer for substrates includes an amino acid polymer, a buffered cross-linking agent, and deionized water (DI $H_2O$). In one example, the amino acid polymer is selected from a neutral or basic amino acid, such as poly l-lysine or poly l-arginine. In another example, the amino acid polymer includes poly l-lsine. In another example, the amino acid polymer includes poly l-lsine of molecular weight of 100,000 or higher. The cross-linking agent can be selected from an aldehyde functional group, a buffered formaldehyde solution or a 10% neutral buffered formalin solution.

3 Claims, 1 Drawing Sheet

CELL ADHESION SOLUTION

RELATED APPLICATION

This application is related to co-pending provisional application of William Alan Fox, Ser. No. 60/224,469, filed Aug. 10, 2000, entitled "CELL ADHESION SOLUTION," and, by this reference, claims the benefit of the priority filing date of the co-pending provisional application.

FIELD OF THE INVENTION

This invention relates to a liquid solution for coating substrates that demonstrates long-term stability cell adhesion properties and, more particularly, to a solution including a cross-linked amino acid polymer for applying to cytological specimen slides.

BACKGROUND OF THE INVENTION

Many diagnostic assays depend on the evaluation of cytological and histological components. One requirement of these evaluations is the adhesion of these components to a solid substrate, such as a glass or plastic microscope slide. Once immobilized by adhesion, these components may be processed further to gain diagnostic information.

Several cytological/histological adhesion reagents have been developed and used in the past, such as albumin, silane, gelatin, and poly l-lysine. Although all are effective adhesive reagents to some degree, their adhesive properties do not remain stable once coated, applied, and dried on a solid substrate. This results in the need to prepare freshly coated slides for optimal routine use.

SUMMARY OF THE INVENTION

The present invention provides a solution of a cross-linked polymer for substrates. The solution includes an amino acid polymer, a buffered cross-linking agent, and deionized water (DI $H_2O$).

In one embodiment, the amino acid polymer, as employed in the invention, is selected from a neutral or basic amino acid, such as but not limited to poly l-lysine or poly l-arginine.

In another embodiment, the amino acid polymer, as employed in the invention, comprises poly l-lsine.

In another embodiment, the amino acid polymer, as employed in the invention, comprises poly l-lsine of molecular weight of 100,000 or higher.

In another embodiment, the cross-linking agent, as employed in the invention, comprises an aldehyde functional group.

In another embodiment, the cross-linking agent, as employed in the invention, comprises a buffered formaldehyde solution.

In one aspect, the present invention provides a cytological/histological adhesion reagent that retains its adhesive properties in a stable fashion when applied to a solid substrate such as a microscope slide.

In another aspect of the invention, it has been found that poly l-lysine is a suitable cytological adhesion reagent when applied and dried on a glass slide, but that its adhesive properties degraded fairly quickly over time. Poly l-lysine is a three dimensional helical polymeric molecule with side chains containing amine functional groups which effect its adhesive properties. With respect to one aspect of the invention, it was postulated that the physical degradation of this three-dimensional helical structure effectively negated the adhesive abilities of these side chain functional groups. In an attempt to retain this adhesive property of the poly l-lysine coated slides, the concept of stabilizing the poly l-lysine molecule structure was considered a viable solution.

In another aspect of the invention, a stabilization process is provided to cross-link the poly l-lysine molecule using formaldehyde. It is believed that the formaldehyde molecules link the functional groups on the end of the side chains back into the molecular framework, thus physically stabilizing the three-dimensional structure.

DETAILED DESCRIPTION OF THE PREFERRED EMBODIMENTS OF THE INVENTION

The present invention generally relates to a cross-linked amino acid polymer solution that can be used to create strong cellular adhesion properties to substrates, such as glass slides, that are stable over a long-term period. This solution allows pre-coating of such slides such that they may be stored for an indefinite period of time until needed.

More particularly, the solutions are aqueous and consist of an amino acid polymer, a cross-linking agent, and a buffering agent to maintain the pH of the solution above 6.0.

In one embodiment, slides coated with the solutions demonstrated stronger cell adhesion properties than currently available solutions and maintained stability up to 31 days.

Figure 1:
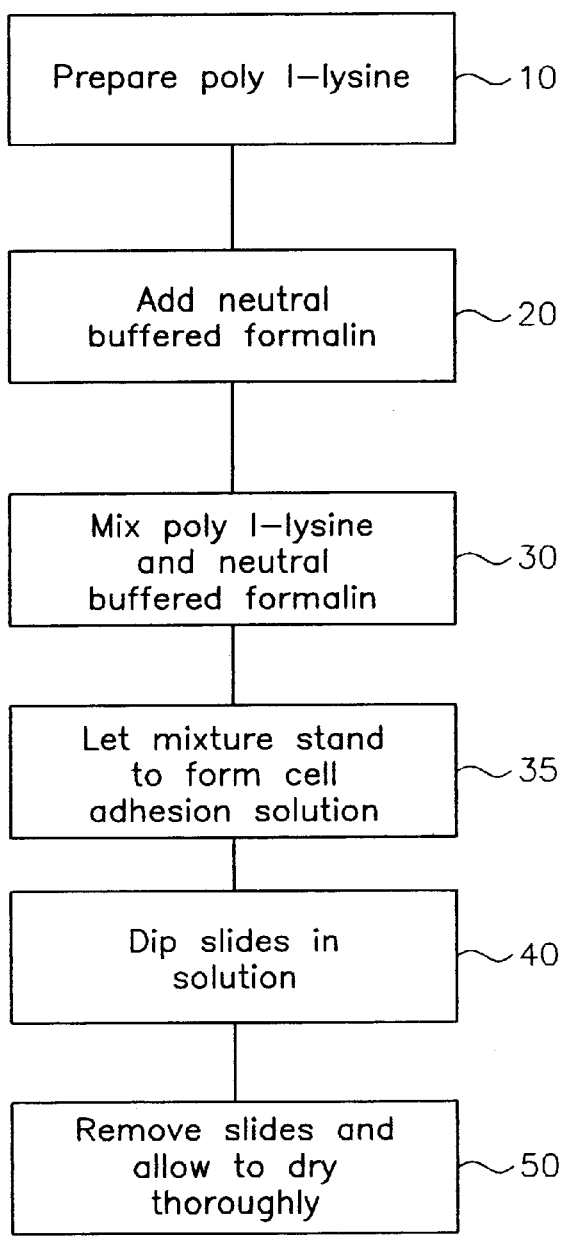
FIG. 1 schematically shows a process flow for an exemplary cell adhesion solution method as employed in accordance with the invention.

Referring now to FIG. 1, there shown schematically is a process flow 100 for an exemplary cell adhesion solution method as employed in accordance with the invention. In one aspect of the invention, the following steps are used:

1. At step 10, a solution of poly l-lysine is prepared,
2. At step 20, neutral buffered formalin is added to the solution of poly l-lysine,
3. At step 30, the resulting solution of poly l-lysine and neutral buffered formalin are mixed,
4. At step 35, the mixed solution is allowed to stand for a predetermined period of time to form a cell adhesion solution,
4. At step 40, slides are dipped in the cell adhesion solution, and
5. At step 50, slides are removed from the mixture and allowed to dry before using.

Materials Used

In implementing the process 100, the following materials were used:

1. Deionized H2O (DI $H_2O$) that is prepared using a standard laboratory Deionized H2O system.
2. Poly L-Lysine that may be obtained, for example, from Sigma Biochemicals company.
3. Neutral Buffered Formalin as may be obtained, for example, from Fisher Scientific company.

In one example, a solution of a cross-linked polymer for substrates included an amino acid polymer, a buffered cross-linking agent, and deionized water (DI $H_2O$). In a preferred embodiment, the amino acid polymer is selected from a neutral or basic amino acid, such as but not limited to poly l-lysine or poly l-arginine. In another embodiment, the amino acid polymer is poly l-1sine. In another embodiment the amino acid polymer is poly l-lsine of molecular weight of 100,000 or higher. In another embodiment the cross-linking agent contains an aldehyde functional group. In another embodiment the cross-linking aldehyde agent is a buffered formaldehyde solution. In another embodiment the cross-linking aldehyde agent is a 10% neutral buffered formalin solution.

In another embodiment of the invention, a solution of a cross-linked polymer that creates strong and stable cell adhesion properties to substrates when applied, includes by volume about 0.03% poly l-lysine in DI $H_2O$; and about 25% neutral buffered formalin. In a more preferred embodiment the solution of a cross-linked polymer includes about 0.015% poly l-lysine in DI $H_2O$ and about 12.5% neutral buffered formalin. In another embodiment the solution of a cross-linked polymer includes about 0.0075% poly l-lysine in DI $H_2O$ and about 6.25% neutral buffered formalin.

EXAMPLES

The following example formulations have proven to be effective.

Formula #1
1. A working stock solution of 0.03% poly l-lysine is prepared by dissolving 0.03 grams of poly l-lysine in 0.100 liters of DI $H_2O$.
2. Equal parts of 0.03% poly l-lysine and neutral buffered formalin are added to the working stock solution of 0.03% poly l-lysine and mixed thoroughly to provide a cell adhesion solution.
3. The cell adhesion solution is allowed to stand for 30 minutes.
4. The cell adhesion solution is transferred to an appropriate container for coating of substrates, such as glass slides.
5. Substrates are dipped into the cell adhesion solution.
6. Substrates are removed from the cell adhesion solution to dry completely (drying may take from 5 minutes to 1 hour, depending on relative humidity),
7. Substrates may be used immediately or stored until needed.

Formula #2
1. A working stock solution of 0.03% poly l-lysine is prepared by dissolving 0.03 grams of poly l-lysine in 0.100 liters of DI $H_2O$.
2. Two parts DI $H_2O$ is added to one part 0.03% poly l-lysine and one part neutral buffered formalin and mixed thoroughly to make the cell adhesion solution.
3. The cell adhesion solution is allowed to stand for 30 minutes.
4. The cell adhesion solution is transferred to an appropriate container for coating of substrates, such as glass slides.
5. Substrates are dipped into the cell adhesion solution.
6. Substrates are removed from the cell adhesion solution to dry completely (drying may take from 5 minutes to 1 hour, depending on relative humidity),
7. Substrates may be used immediately or stored until needed.

In experiments conducted at TriPath Imaging, Inc. of Burlington, N.C., slides processed with an exemplary cell adhesion solution method as employed in accordance with the invention were compared against conventionally processed slides. A single cervical cytological sample was processed on all slides in the experiment. Two slides were coated using a known formula. It was noted that slides freshly prepared with the known formula demonstrate good cellular adhesion, but diminished in adhesion over time. However, slides prepared with two embodiments of the cell adhesion solution made in accordance with the present invention, namely formula #1 and formula #2, demonstrated superior adhesion. This despite the observation that the amino acid polymer concentration decreased two and four fold for formula #1 and formula #2 respectively.

Figure 2:
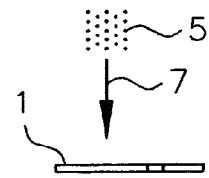
FIG. 2 shows schematically a process for depositing a cytological specimen on a slide processed with an exemplary cell adhesion solution method as employed in accordance with the invention.

Referring now to FIG. 2, FIG. 2 shows schematically a process for depositing a cytological specimen 5 on a slide 1 processed with an exemplary cell adhesion solution method as employed in accordance with the invention. The cytological specimen 5 may be deposited using standard methods as generally indicated by arrow 7. The cytological specimen 5 may comprise, but is not limited to, a cervical cytological sample.

Figure 3:
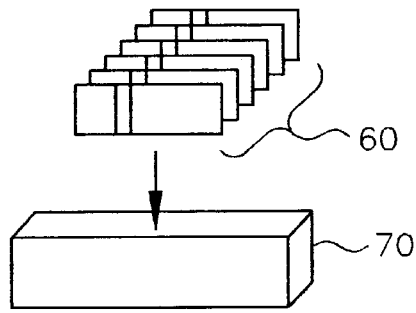
FIG. 3 shows schematically a set of slides processed with an exemplary cell adhesion solution method as employed in accordance with the invention being stored for future use.

FIG. 3 shows schematically a set of slides 60 processed with an exemplary cell adhesion solution method as employed in accordance with the invention being stored for future use in a storage bin 70.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different materials and structural configurations, and that various modifications, both as to materials and structural configurations and operating procedures, may be accomplished without departing from the true spirit and scope of the present invention.

What is claimed is:

1. A solution of a cross-linked polymer that creates strong and stable cell adhesion properties to substrates when applied, said solution comprising, by volume:
    a) where said whole solution includes from 0.015% up to 0.03% poly l-lysine in DI $H_2O$; and
    b) where said whole solution includes from 12.5% up to 25% neutral buffered formalin.

2. The solution of claim 1 where said poly l-lysine has a molecular weight of 100,000 or higher.

3. A solution of a cross-linked polymer that creates strong and stable cell adhesion properties to substrates when applied, said solution comprising, by volume:
    a) where said whole solution includes from 0.0075% up to 0.03% poly l-lysine in DI $H_2O$, where said poly l-lysine has a molecular weight of 100,000 or higher; and
    b) where said whole solution includes from 6.25% up to 25% neutral buffered formalin.

* * * * *

UNITED STATES PATENT AND TRADEMARK OFFICE
CERTIFICATE OF CORRECTION

PATENT NO. : 6,657,003 B2
DATED : December 2, 2003
INVENTOR(S) : Fox

It is certified that error appears in the above-identified patent and that said Letters Patent is hereby corrected as shown below:

Title page,
Item [56], References Cited, OTHER PUBLICATIONS, change "Poblisher" to
-- publisher --.
Item [57], ABSTRACT,
Lines 6 and 8, change "poly l-lsine" to -- poly l-lysine --.

Column 1,
Lines 44 and 46, change "poly l-lsine" to -- poly l-lysine --.

Column 3,
Lines 5 and 6, change "poly l-lsine" to -- poly l-lysine --.

Signed and Sealed this

Third Day of February, 2004

JON W. DUDAS
*Acting Director of the United States Patent and Trademark Office*